United States Patent [19]

Kanno et al.

[11] 4,106,987
[45] Aug. 15, 1978

[54] METHOD OF ISOMERIZING GLUCOSE TO FRUCTOSE

[75] Inventors: Tomoei Kanno, Okegawa; Hiroaki Watanabe, Yokohama; Shohachiro Sano, Ageo, all of Japan

[73] Assignee: Showa Sangyo Co. Ltd., Tokyo, Japan

[21] Appl. No.: 757,211

[22] Filed: Jan. 6, 1977

[30] Foreign Application Priority Data

Jan. 8, 1976 [JP] Japan .................................. 51-1789
Jan. 16, 1976 [JP] Japan .................................. 51-4462

[51] Int. Cl.² ............................................. C12D 13/00
[52] U.S. Cl. ..................................... 195/31 F; 195/63
[58] Field of Search .......... 195/31 F, 63, 68, DIG. 11

[56] References Cited

U.S. PATENT DOCUMENTS

| | | | |
|---|---|---|---|
| 3,972,776 | 8/1976 | Vieth et al. | 195/65 |
| 3,980,521 | 9/1976 | Amotz et al. | 195/68 |
| 4,001,082 | 1/1977 | Tsumura et al. | 195/31 F |

OTHER PUBLICATIONS

Toda et al., Biotechnology and Bioengineering, vol. XVII, pp. 481–497, (1975).

*Primary Examiner*—Lionel M. Shapiro
*Attorney, Agent, or Firm*—Hans Berman

[57] ABSTRACT

An immobilized glucose isomerase is obtained by mixing microbial cells of the microorganism having glucose isomerase activity with an aqueous solution of a natural water insoluble gel-forming substance. Glucose is isomerized to fructose by contacting an aqueous solution of glucose with said immobilized glucose isomerase more favorably than the usual isomerization method.

3 Claims, No Drawings

METHOD OF ISOMERIZING GLUCOSE TO FRUCTOSE

This invention relates to immobilized glucose isomerase and particularly to the preparation and use thereof. An enzyme so-called glucose isomerase can be obtained from various microorganisms belonging to genus Streptmyces, Lactobacillus etc., and has been used widely in commercial glucose isomerization processes.

The microbial cells of the microorganisms having glucose isomerase activity are used usually only in batch process for glucose isomerization where cells of microorganisms are suspended in an aqueous solution of glucose and glucose is isomerized to fructose under the presence of magnesium sulfate at pH 7.0, 70° C in the reaction mixture. After reaction of about 70 hours about 45% of glucose is converted into fructose and the cells are separated from the mixture by filtration. The filtered solution is bleached with active carbon and is refined furtherly with ion exchanger.

In this process, however, there is an extreme trouble in refining the resultant sugar solution, since the solution is coloured by the formation of psicose, decomposed product of glucose, during the reaction of 70 hours.

In continuous glucose isomerization process, an immobilized enzyme preparation can be used which is prepared by adsorbing or combining the extracted and purified enzyme on or with a water-insoluble carrier. Various substances have been disclosed as a carrier for immobilization of purified enzyme including chemical substances such as glutaraldehyde, acrylamide etc. In fact, most of them, however, cannot be used in the commercial process in view of the legislation for manufacturing foods. Carrier is practically limited to a substance allowed under Food Regulation Law.

The enzyme activity of the above immobilized enzyme preparation decreases gradually in the course of reaction. The activity is no longer retained after the use of 100 hours. This decrease is generally covered by the complicated steps such as slow-down of the flow rate and elevation of the temperature of the reaction solution. Thus the production cost increases due to the above unreasonable operation and the cost for preparing the immobilized purified enzyme.

The object of the present invention is to provide an immobilized glucose isomerase comprising microbial cells having isomerase activity and the natural water-insoluble gel forming substances and the preparation thereof. It is not harmful in the production of foods.

Another object of the invention is to provide a method for isomerizing glucose to fructose using the above immobilized glucose isomerase.

Microbial cells are used as a source of glucose isomerase in the present invention. Glucose isomerase is produced and accumulated during cultivation in the cells of the microorganisms belonging to genus such as Lactobacillus, Pseudomonas, Leuconostoc, Streptmyces, Aerobacter etc. These cells are separated from the culture medium and are immobilized with natural water insoluble gel-forming substance which is at least one member selected from the group consisting of agar-agar, gelatine, collagen, pectin, flour of Amorphophalus Konjac K. Koch, locust bean gum, casein, wheat flour, wheat gluten, soy protein, egg white, tannin, persimmon tannin and starch.

These substances form a water-insoluble gel by merely adding water to them, heating and cooling the aqueous solution, adding the suitable coagulant to the solution or by evaporating water from the solution.

Immobilization is carried out by mixing cells with the aqueous solution of the gel forming substances and the mixture is converted into water insoluble gel. Decrease of enzyme activity during immobilization is small.

Isomerization of glucose to fructose is carried out in the chambers or columns containing the immobilized glucose isomerase by contacting an aqueous solution of glucose with said immobilized glucose isomerase. Since the reaction solution after isomerization is less colored than the usual cell contacting method and the enzyme activity still remains even after 120 hrs, isomerization process is carried out more favourably than the conventional method.

EXAMPLE 1

1500g of commercial cells of glucose isomerase ("Godo A.G.I.," Enzyme activity: 1300 units/g, sold by Godo Shusei Co., Ltd.) was mixed with 600 ml of 15% aqueous solution of commercial gelatine containing 0.1 mole of magnesium sulfate, added with 75g commercial tannin, extending the mixture in thin layer less than 2 mm thickness, leaving at room temperature for 2 days, and an immobilized glucose isomerase was obtained. It was washed with cool water at 20° C to remove unreacted tannin. Total enzyme activity of the product was $150 \times 10^4$ units which was 76.9% of the initial enzyme activity.

Continuous glucose isomerization was carried out using this immobilized glucose isomerase in the reaction chambers under the conditions shown in Table 1.

Table 1

| Aqueous glucose solution: | |
|---|---|
| Solid matter | 46% |
| glucose | 93.5% of solid matter |
| additive | magnesium sulfate ($MgSO_4 \cdot 7H_2O$) 0.1% (W/V) |
| pH | 7.5 (adjusted with phosphate buffer) |
| Rate of flow: | 26 ml/min. |
| Temperature: | 65° C |

The decrease of enzyme activity during the processing was measured and the ratio of isomerization was shown in Table 2.

Table 2

| Processing time (hours) | 24 | 72 | 120 | 168 |
|---|---|---|---|---|
| Ratio of isomerization (%) | 47 | 45 | 45 | 32 |

EXAMPLE 2

300g of commercial cells of glucose isomerase ("Godo A.G.I.," enzyme activity: 1030 units/g, sold by Godo Shusei Co., Ltd.) was mixed with agar-agar solution which was prepared by dissolving 140g of powdered agar-agar into 200 ml of water at 90° C and the mixture was cooled to about 70° C. It was frozen in a freezer at −15° C, thawed after freezing then the immobilized glucose isomerase was obtained. The total enzyme activity of the product was $24 \times 10^4$ units which was 77.7% of the initial enzyme activity. Continuous glucose isomerization was carried out with this immobilized enzyme in the chambers as in Example 1 under the conditions shown in Table 3.

Table 3

| Aqueous glucose solution: |
|---|

Table 3-continued

| the same as in Example 1 | |
|---|---|
| Rate of flow: | 8 ml/min. |
| Temperature: | 60° C |

The decrease of enzyme activity during the processing was measured and the ratio of isomerization was shown in Table 4.

Table 4

| Processing time (hours) | 24 | 72 | 120 |
|---|---|---|---|
| Ratio of isomerization (%) | 45 | 45 | 38 |

N.B.
1. Glucose isomerase activity:
   Glucose isomerase activity of one unit equals to an amount of the enzyme which produces one milligram fructose by reacting the enzyme with 0.1 mole glucose solution (adjusted at pH 7.0 with 0.05 mole phosphate buffer) containing 0.1 mole magnesium sulfate at 70° C for 1 hour.
2. Measurement of glucose content:
   "Glucostat" method.
3. Measurement of fructose content:
   Cystein-Carbazole method.
4. Ratio of isomerization (%) = fructose/glucose + fructose × 100

In the isomerization process, a small amount of glucose isomerase leaks from the immobilized cells and escapes unused in the solution. The present invention provides the columns filled with anion exchange resin, through which the isomerized solution passes in order to recover the leaked isomerase in said resin. Favourable results are obtained by using the columns of anion exchange resin in the isomerization procedure.

EXAMPLE 3

300g of commercial cells of glucose isomerase, (trade name and activity is the same as in Example 2) was mixed with 150 ml of aqueous solution of glucose containing 48% of glucose and 6g of magnesium sulfate and 75g of fullers earth are added to the mixture. The resultant mixture was mixed with gel formed by dissolving 15g of flour of Amorphophalus Konjak in 300 ml of hot water and by heating the mixture at 65° C for 1 hour. Thus the immobilized glucose isomerase is obtained.

Continuous glucose isomerization was carried out using this immobilized glucose isomerase in the reaction chambers and the isomerized solution was introduced into 3 cm × 6 cm jacketed column filled with 300 ml of anion exchange resin (Amberite IRA-401, Cl type, sold by Organo Co., Ltd.). The condition and the results of the experiment are described below:

| Aqueous glucose solution | |
|---|---|
| solid matter | 48% |
| glucose | 94% of solid matter |
| additive | $MgSO_4 \cdot 7H_2O$ 0.1% (W/V) |
| pH | 7.5 (adjusted with phosphate buffer) |
| Rate of flow: | 8 ml/min. |
| Temperature: | 60° C |

Results of the experiment:

| Processing time (hours) | 24 | 120 | 240 | 360 |
|---|---|---|---|---|
| Ratio of isomerization (%) | 45 | 45 | 40 | 32 |

Results of the experiment without using anion exchange resin

| Processing time (hours) | 24 | 120 | 240 |
|---|---|---|---|
| Ratio of isomerization (%) | 45 | 40 | 28 |

EXAMPLE 4

100g of immobilized glucose isomerase produced by NOVO INDUSTRIES A.G. (Sweetzyme, 150 International glucose isomerase unit/g, sold by Mitsui Bussan Co., Ltd.) was filled in the jacketed glass column of 3 cm × 120 cm.

The aqueous glucose solution was introduced into this column, passed through it and then introduced into the second column containing 200 ml of used anion exchange resin (Amberite IRA-411, Cl type, sold by Organo Co., Ltd.).

The continuous isomerization was carried out under the condition as in Example 3 except the rate of flow of 5 ml/min.

Results of the experiment:

| Processing time (hours) | 24 | 120 | 240 |
|---|---|---|---|
| Ratio of isomerization (%) | | | |
| without column of resin | 35 | 38 | 22 |
| using two columns | 35 | 45 | 40 |

What is claimed is:
1. A method of isomerizing glucose to fructose which comprises contacting a stream of an aqueous glucose solution with a hydrogel of an edible substance and thereafter with an anion exchange resin, said hydrogel containing dispersed cells of a microorganism having glucose isomerase activity.
2. A method as set forth in claim 1, wherein said substance is at least one member selected from the group consisting of agar-agar, gelatine, collagen, pectin, flour of Amorphophalus Konjac K. Koch, locust bean gum, casein, wheat gluten, soy protein, egg white, tannin, persimmon tannin, wheat flour and starch.
3. A method as set forth in claim 1, wherein said microorganism is at least one strain belonging to genus Lactobacillus, Pseudomonas, Leuconostoc, Streptomyces or Aerobacter.

* * * * *